United States Patent
Wehowski

(10) Patent No.: US 12,147,332 B2
(45) Date of Patent: Nov. 19, 2024

(54) METHOD AND SYSTEM FOR STORING MEASUREMENT DATA DETECTED BY A SENSOR DEVICE AND INDICATIVE OF AN ANALYTE IN A SAMPLE OF A BODILY FLUID

(71) Applicant: Roche Diabetes Care, Inc., Indianapolis, IN (US)

(72) Inventor: Frederic Wehowski, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 6 days.

(21) Appl. No.: 17/935,094

(22) Filed: Sep. 24, 2022

(65) Prior Publication Data
US 2023/0016092 A1 Jan. 19, 2023

Related U.S. Application Data

(63) Continuation of application No. PCT/EP2021/057331, filed on Mar. 23, 2021.

(30) Foreign Application Priority Data

Mar. 25, 2020 (EP) .................................. 20165701

(51) Int. Cl.
G06F 12/02 (2006.01)
G01N 33/49 (2006.01)
H03M 7/30 (2006.01)

(52) U.S. Cl.
CPC .......... *G06F 12/0246* (2013.01); *H03M 7/30* (2013.01); *G01N 33/492* (2013.01)

(58) Field of Classification Search
CPC ......... G06F 12/0246; G06F 2212/1016; G06F 2212/1048; G06F 12/04; H03M 7/30; G01N 33/492; G16H 10/60
See application file for complete search history.

(56) References Cited

U.S. PATENT DOCUMENTS 5,819,740 A * 10/1998 Muhlenberg ........ H03M 7/3053
607/9
5,836,982 A * 11/1998 Muhlenberg ............ H03M 7/42
607/9

(Continued)

FOREIGN PATENT DOCUMENTS

EP 2 183 671 A1 5/2010
TW 201515633 A 5/2015

OTHER PUBLICATIONS

International Search Report and Written Opinion of the International Searching Authority, PCT/EP2021/057331, May 7, 2021, 11 pages.

*Primary Examiner* — Jared M Bibbee
(74) *Attorney, Agent, or Firm* — Bose Mckinney and Evans LLP

(57) ABSTRACT

A method for storing measurement data detected by a sensor and indicative of an analyte in a body fluid sample using a system having a processor and a memory. First and second measurement data indicative of first and second measurement values measured by a sensor, respectively, are provided. A relative measurement value is determined by the processor and is indicative of a value difference between the first and second measurement values. The first measurement value is stored in a first storage area having a first storage size in the memory. The relative measurement value is stored in a second storage area having a second storage size in the memory that is smaller than the first storage size. An indicator is also stored in the memory and is assigned to the relative measurement storage data in the memory and is indicative of a characteristic of the relative measurement storage data.

11 Claims, 3 Drawing Sheets

(56) References Cited

U.S. PATENT DOCUMENTS

| | | | | |
|---|---|---|---|---|
| 9,222,951 | B2* | 12/2015 | Schmitt | G01N 35/00693 |
| 2006/0189926 | A1* | 8/2006 | Hall | A61B 5/150213 |
| | | | | 600/316 |
| 2007/0270672 | A1* | 11/2007 | Hayter | A61B 5/150526 |
| | | | | 600/309 |
| 2009/0319872 | A1* | 12/2009 | Alrod | G11C 16/26 |
| | | | | 714/E11.038 |
| 2016/0106339 | A1* | 4/2016 | Behzadi | G16H 20/10 |
| | | | | 600/302 |
| 2017/0235911 | A1* | 8/2017 | Chen | G16H 10/60 |
| | | | | 705/2 |
| 2020/0217814 | A1* | 7/2020 | Pankalla | C12Q 1/32 |
| 2021/0100951 | A1* | 4/2021 | Chase | G01C 19/02 |
| 2021/0137430 | A1* | 5/2021 | Haase | A61B 5/6862 |

\* cited by examiner

METHOD AND SYSTEM FOR STORING MEASUREMENT DATA DETECTED BY A SENSOR DEVICE AND INDICATIVE OF AN ANALYTE IN A SAMPLE OF A BODILY FLUID

RELATED APPLICATIONS

This application is a continuation of PCT/EP2021/057331, filed Mar. 23, 2021, which claims priority to EP 20 165 701.2, filed Mar. 25, 2020, both of which are hereby incorporated herein by reference.

BACKGROUND

The present disclosure refers to a method and a system for storing measurement data detected by a sensor device and indicative of an analyte in a sample of a bodily fluid.

Common systems measuring analytes in a sample of a bodily fluid, such as continuous glucose monitoring (CGM) systems, run one or several weeks with the same device including a chemical sensor, which is put under the skin of a patient. Such systems produce relevant values to be stored, e.g., a glucose value, every one to five minutes. The values are often recorded in a memory. By recording the values in a memory, it is possible to ensure that these values are not lost even if the communication with a handheld device is interrupted. Additionally, it is possible to analyze the recorded values in the case of a problem in order to understand why the device did not perform as expected.

In general, the device, which is placed, for example, under the skin of a patient, not only stores the measurements of the BG value, but also records other parameters (e.g., the current flowing into the sensor, the temperature, the regulation voltage of a potentiostat, errors, the battery voltage, the impedance of the sensor, etc.) in the memory. By storing such a variety of data in the memory, the storing capacity of the memory can quickly be exhausted. Moreover, the recorded parameters, for example, the BG values, often are medians or averages of raw measurements made once per second, which are stored in the memory together with their standard deviation. However, storing many data can be an advantage to help analyzing unforeseen problems.

An exemplary typical CGM system that stores 16 bytes per minute of measurement data ends up with a total of 315 kBytes after two weeks of functioning. Taking into account that electronic devices related to this system are disposable and that the cost therefore must be low, 315 kBytes is a huge amount of data. Modern CGM systems are merely used for the life of the sensor or a few months. However, the device must contain enough storage memory to store all the relevant values, although the cost of the device must be low.

The data can be stored in RAM or permanent memory, for example, Flash or EEPROM. The disadvantage of the RAM storage is that the cost per bit is higher than that of permanent memory, and in case of battery failure, the information are lost forever. However, the RAM memory can be written and erased as required and very fast. Flash and EEPROM do need more time to be written and need more energy. Besides, Flash and EEPROM are organized in pages of several kBytes, and in many cases it is impossible to erase less than a full page. An erase operation for Flash and Eeprom also requires time (on a scale of milliseconds) and energy.

In order to save space in the memory the stored data can be compressed lossless. Lossless compressed data can be decompressed intact and completely. In comparison, lossy data compression is irreversible, and data cannot be decompressed intact and completely after such a compression. Lossy compression algorithm is used, for example, in image or sound compression as in: mp3, jpeg, mp4, H264, etc. Lossless algorithms are used, for example, in the zip format or in image format as in png or gif.

Most of the lossless algorithms are using a dictionary, i.e., they first analyze the entire data set with respect to a pattern, which is found very often in the data set, and then this pattern is replaced with something shorter. For example, if the dataset is a text in which the words "at the present time" are used frequently, these words can be replaced by a sequence of one or two bytes. This sequence can be written into the dictionary and can be used to retrieve the original text during decompression.

Common algorithms for compressing data, such as the algorithm mentioned above, require a lot of time due to the way they are working. Namely, it must be waited until a large block of data is recorded before the compressing algorithm can be started. It is not possible to compress "on-the-fly," i.e., to compress the data at the time they are produced. Moreover, these algorithms need too much memory space, so that in the end, there is no advantage left for the use cases of interest, such as CGM systems.

U.S. Pat. No. 9,222,951 B2 discloses a method for operating measuring equipment for detecting an analyte in a bodily fluid by means of a continuously measuring blood glucose sensor. A calibration method is carried out for the prospective calibration of the measuring equipment. At least three calibration points are detected in the calibration method, wherein each calibration point comprises a measurement signal from the measuring equipment and a reference value of an associated reference measurement. A plurality of possible slopes are established between the calibration points. At least one robust estimation method using a formation of at least one median is used to determine a probable slope from the plurality of possible slopes. Furthermore, a measurement is carried out. During the measurement and using the probable slope, a concentration of the analyte in the bodily fluid is deduced from a measurement signal from the measuring equipment and the probable slope.

SUMMARY

The present disclosure provides improved technology for a method and a system for storing measurement data detected by a sensor device and indicative of an analyte in a sample of a bodily fluid. (Bodily fluid and body fluid are used interchangeably herein.)

According to one aspect, a method for storing measurement data detected by a sensor device and indicative of an analyte in a sample of a bodily fluid is provided. The method comprises, in a system having a processor and a memory: providing first measurement data indicative of a first measurement value for an analyte in a sample of a bodily fluid measured by a sensor device, providing second measurement data indicative of a second measurement value for the analyte in the sample of the bodily fluid measured by the sensor device, determining a relative measurement value by the processor, the relative measurement value being indicative of a value difference between the first measurement value and the second measurement value, providing first measurement storage data in the memory, comprising storing the first measurement value being assigned to a first storage area having a first storage size in the memory, providing relative measurement storage data in the memory, comprising storing the relative measurement value in the memory, the relative measurement storage data being assigned to a second storage area having a second storage size in the memory which is smaller than the first storage size, and storing an indicator in the memory, the indicator being assigned to the relative measurement storage data in the memory and indicative of a characteristic of the relative measurement storage data.

According to another aspect, a system for storing measurement data detected by a sensor device and indicative of an analyte in a sample of a bodily fluid is provided. The system has a processor and a memory. Further, the system is configured to: provide first measurement data indicative of a first measurement value for an analyte in a sample of a bodily fluid measured by a sensor device, provide second measurement data indicative of a second measurement value for the analyte in the sample of the bodily fluid measured by the sensor device, determine a relative measurement value by the processor, the relative measurement value being indicative of a value difference between the first measurement value and the second measurement value, provide first measurement storage data in the memory, comprising storing the first measurement value being assigned to a first storage area having a first storage size in the memory, provide relative measurement storage data in the memory, comprising storing the relative measurement value in the memory, the relative measurement storage data being assigned to a second storage area having a second storage size in the memory which is smaller than the first storage size, and store an indicator in the memory, the indicator being assigned to the relative measurement storage data in the memory and indicative of a characteristic of the relative measurement storage data.

The storage size assigned to the indicator may be one or more bits.

The second measurement value may not be stored in the memory. The second measurement value can be determined from the first measurement value stored in the memory and the relative measurement value. In addition, further or a plurality of relative measurement values can be stored in the memory. The further or the plurality of relative measurement values may be indicative of further or a plurality of measurement values. The plurality of measurement values can be determined successively from the first measurement value and the plurality of relative measurement values. In particular, a specific measurement value assigned to a corresponding relative measurement value stored in the memory can be reconstructed from this corresponding relative measurement value and the first measurement value in combination with the relative measurement values stored therebetween. Hence, the first measurement storage data may provide a starter value for the plurality of measurement values to be stored.

The measurement data may comprise, for example, time in seconds since the start, a median, indicative of the current flowing into the sensor, a standard deviation, a sensor voltage median, a battery voltage, a temperature of the sensor device, a glucose value, as well as an error and event flags.

Further sensor data may be provided with the measurement data to be stored. For example, sensor data from a pressure sensor may be provided with the measurement data such as sensor data indicative a mechanical pressure applied externally to the sensor device for detecting the first measurement data indicative of the first measurement value for the analyte in the sample of a bodily fluid. For example, the first measurement data may be detected by a continuous glucose monitoring (CGM) sensor for measuring glucose concentration in the interstitial fluid (ISF). In addition or as an alternative, further sensor data may be received for storing from an orientation sensor, the sensor data being indicative of whether a patient for whom the first measurement data are collected is standing or lying.

The method may comprise storing an additional indicator in the memory, the additional indicator being assigned to the first measurement storage data in the memory and indicative of a characteristic of the first measurement storage data.

The providing of the first measurement storage data may comprise storing an absolute value of the first measurement value. In the memory, the additional indicator may be configured to indicate that the first measurement storage data comprises the absolute value of the first measurement value. In addition or alternatively, the additional indicator can indicate that the first measurement storage data is not compressed. In an exemplary embodiment, the additional indicator may be stored by one bit, e.g., if the bit is 0, it is indicated that the assigned first measurement storage data is not compressed or alternatively, if the bit is 1, it is indicated that the assigned first measurement storage data is compressed. In another exemplary embodiment, the additional indicator can be stored by more than one (data) bit. Thus, the storage size assigned to the additional indicator stored in the memory can be one or more bits.

The storage of an absolute value measured by the sensor device must not be limited to the first measurement storage data. Further absolute measurement storage data may be provided in the memory, comprising storing the absolute value of the further measurement values. To each of the absolute measurement storage data a corresponding additional indicator can be assigned and stored in the memory.

The method may further comprise storing the first measurement value, the relative measurement value, and the indicator bit by bit in a consecutive order of data bits. The indicator may be stored before storing the relative measurement value in the order or arrangement of (data) bits. Alternatively, the indicator may be stored after storing the relative measurement value. The indicator may be stored between the first storage area assigned to the first measurement value and the second storage area assigned to the relative measurement value. The second storage area assigned to the relative measurement value can be smaller than the first storage area assigned to the first measurement value. In other words, the relative measurement value can be stored by less bits than the first measurement value. Thus, the storage size of the relative measurement storage data can be smaller by one or more bits than the storage size of the first measurement storage data. Storing the first measurement value may comprise storing the absolute measurement value.

The second storage size may be smaller by one or more bits compared to the first storage size. By storing measurement data in the second storage area having the second storage size instead of storing measurement data in the first storage area having the first storage size, a smaller number of bits may be required. The storage size of the relative measurement data may be smaller than the storage size of the second measurement data. By storing the relative measurement value in the second storage area instead of storing the second measurement value, in particular an absolute value of the second measurement value, a smaller number of bits may be required. Thus, the storage size assigned to the measurement data in the memory may be reduced. Hence, a compression of the required storage size may be performed.

Providing the second measurement storage data may comprise providing and/or storing the absolute value of the second measurement value. Instead of storing the absolute value of the second measurement value, the relative measurement value in combination with the absolute value of the first measurement value can be stored in the memory. After such storing, the absolute value of the second measurement value can be reconstructed from the stored relative measurement value in combination with the absolute value of the first measurement value. By this reconstruction the absolute value of the second measurement value can be determined exactly. Hence, the absolute value of the second measurement value can be reconstructed lossless.

The indicator assigned to the relative measurement storage data may be indicative of a number of data bits assigned to the second storage size in the memory. The number of bits assigned to the second storage size may be dependent on the relative measurement value. In particular, the number of bits assigned to the second storage size may be dependent on the size of the relative measurement value. The higher the size of the relative measurement value the higher may be the number of bits assigned to the second storage size. To determine the size of data bits assigned to the second storage size in the memory one or several thresholds may be provided.

In one exemplary embodiment one threshold may be provided. Thus, in a first case where the relative measurement value is smaller than or smaller or equal to the one threshold, the second storage size in the memory may be assigned to a first number of bits. In a second case where the relative measurement value is greater than or grater or equal to the one threshold, the second storage size in the memory may be assigned to a second number of bits. If one thresholds is provided, the size of the indicator may be one bit. An indicator of the size of one bit can indicate two states (0 and 1). Thus, the two cases stated above can be indicated by the indicator. The second number of bits can be greater than the first number of bits.

In another exemplary embodiment a first and a second threshold are provided. Thus, in a first case where the relative measurement value is zero, e.g., the absolute value of the first measurement value is identical to the absolute value of the second measurement value, the size of data bits assigned to the second storage size in the memory may be zero. The first case is optional. In a second case where the relative measurement value is greater than zero and smaller than or smaller or equal to the first threshold, the second storage size in the memory may be assigned to a first number of bits. In a third case where the relative measurement value is greater than or grater or equal to the first threshold and smaller than or smaller or equal to the second threshold, the second storage size in the memory may be assigned to a second number of bits. The second number of bits can be greater than the first number of bits. In a fourth case where the relative measurement value is greater than or grater or equal to the second threshold, the second storage size in the memory may be assigned to a third number of bits. The third number of bits can be greater than the second number of bits. In the fourth case, the absolute value of the second measurement value may be stored in the memory. If two thresholds are provided, the size of the indicator may be two bits. An indicator of the size of two bits can indicate four states (00, 01, 10, and 11). Thus, the four cases stated above can be indicated by the indicator.

The exemplary embodiments with one or two thresholds stated above apply mutatis mutandis to further embodiments, wherein such thresholds are provided. For example, more than two thresholds may be provided. The size of the indicator can be adapted to the number of thresholds provided and may be one or more bits.

The indicator assigned to the relative measurement storage data may be indicative of a data compression characteristic of the relative measurement storage data. The indicator may indicate whether the relative measurement storage data is smaller than the second measurement data. In particular, the indicator may indicate whether the relative measurement value is smaller than the second measurement value. Further, the indicator may indicate whether the relative measurement storage data is compressed or not. Alternatively or additionally, the indicator may indicate to which extend, e.g., by which factor, the relative measurement storage data is compressed.

The indicator may be provided in a header information in the memory. Further, the additional indicator may be provided in a header information in the memory. At the beginning of the memory, the header may be provided. The header may comprise first measurement data. In particular, the header may comprise first measurement values. The header may comprise the absolute values of the first measurement values. One or more than one headers can be provided. The whole memory can be split into several pages (for example, matching the page size of a Flash or EEPROM memory). Each page may contain an assigned header. The headers assigned to each page can be provided at the beginning of the page. In the case where the headers are assigned to each page, every page can be decoded independently. In other words, the second measurement data, in particular the absolute values of the second measurement values of a specific page, can be determined from the relative measurement data, in particular the relative measurement values, in combination with the header assigned to the specific page independently of other pages. The header can also contain more information, for example, the serial number of the device or the start time and date. Thus each page can be truly independent and identifiable.

In an exemplary embodiment the measurement data comprise, for example, eight measurement values. The first measurement storage may comprise the eight measurement values. The second or the relative measurement data may comprise the eight measurement values. The further measurement data or the further relative measurement data may comprise values indicative of the eight measurement values. Each minute the measurement data comprising eight measurement values may be detected by a sensor. Further, each minute the measurement data comprising eight measurement values may be stored in the memory as relative measurement values or as absolute measurement values. The system having a processor and a memory and the sensor device may be powered by a lithium battery with about 1 volt, alternatively with about 1.5 volt, in particular with a voltage between about 1 volt and about 3 volt.

The eight measurement values may be selected from the following group: time in seconds since the start, a median of a current flowing into the sensor, a standard deviation, a sensor voltage median, a battery voltage, temperature of the device, BG value in mg/dl, alternatively in kg/l, as well as an error and event flags (each value being stored by, e.g., 10 bits, in particular by a number of bits in the range of 6 to 22, alternatively stored by more than 22 bits).

In an example, the measurement data may have a size of 96 bits, alternatively 10 bits to several kBits, alternatively more than 1 kBit. The measurement data may be provided every minute, alternatively every second, in particular every hour. The absolute values of the eight measurement values corresponding to the first measurement data may be stored as the header. The eight values may be stored bit by bit in a consecutive order of data bits in the memory. For decompression, values in the header may be provided as the starter values. The second measurement data, in particular the absolute value of the second measurement value can be determined by the relative measurement data and the starter values in the header. Further measurement data, in particular the absolute values of the further measurement values can be determined by the further relative measurement data and the starter values in the header. The decompression may be a determining of the relative or the further relative measurement data.

By storing the relative measurement data and/or the further relative measurement data instead of the second measurement data and/or the further measurement data the measurement data stored may be compressed. Stored measurement data that are compressed may have a smaller size than measurement data that are decompressed. A compression algorithm may be different and may be adapted to each measurement value. The algorithm may at least add one bit in front of each measurement value stored, depending on the rate of compression. These bits may be header bits.

In one embodiment the measurement data may be "Time in second since the start." A new measurement value may be stored every 60 seconds. Only one header bit, e.g., the additional indicator or the indicator, may be stored. This bit, e.g., corresponding to the additional indicator, may be 1 indicative of the characteristic of the first measurement data, in particular of the further measurement values of the further absolute measurement values. If the first bit is 1, it may mean that the 21 following bits contain the first measurement data or the further measurement value, in particular the absolute value of the first measurement value or of the further measurement value, e.g., the information "Time in second since the start". If the first bit is a 0, it may mean the relative measurement data, or alternatively, one of the further relative measurement is stored. In this example the relative or the further relative measurement data may have the size of zero. Thus, the indicator can indicate that "Time in second since the start" is equal to the last value plus 60 seconds.

In a further embodiment, a median can be stored on 12 bits, from 0 to 100 nA in steps of 25 pA. 6 bits may be provided as the first storage area, thus may correspond to +31/−32 LSB (bit numbering) and to a range of +775 to −800 pA. The first threshold may comprise two limiting values being +775 and −800 pA. If the relative measurement value is in-between the limiting values, the header bit is set to 0 and may be the indicator. In this case the relative measurement value may be stored in the memory. If the relative measurement value is not in-between the limiting values, the header bit is set to 1 and may be the additional indicator. In this case the absolute value of a first or the further measurement data may be stored in the flowing 12 bits being the second storage area. More than one header bit and more than one threshold may be provided.

In another exemplary embodiment two header bits may be provided. If the header bits are 00, e.g., being the indicator, it may mean that the difference between the first measurement value and the second measurement value is zero. Thus, 2 bits may be stored in the memory instead of 12 bits. If the header bits are 01, e.g., being a further indicator, it may mean that the relative measurement value is stored on the next 4 bits with a possible range of +7/−8 LSB. Thus, 6 bits may be stored in the memory instead of 12 bits. If the header bits are 10, e.g., being a second further indicator, it may mean that the relative measurement value is stored on the next 7 bits with a possible rage of +70(63+7)/−71(64+8) LSB. Thus, 9 bits may be stored instead of 12 bits. If the header bits are 11, e.g., being the additional indicator, it may mean that the absolute value of first or the further measurement values is stored on the next 12 bits. In this case, the stored value may have no dependence on other measurement data stored.

All the measurement data can be stored applying the method proposed. For each measurement data, a statistical analysis can be conducted on real examples to find the optimal method of storing measurement data. For example, it may be determined how many header bits may be used for the measurement data and the optimal thresholds may be selected.

The examples disclosed above with regard to the method for storing measurement data detected by a sensor device and indicative of an analyte in a sample of a bodily fluid may apply to the system mutatis mutandis.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
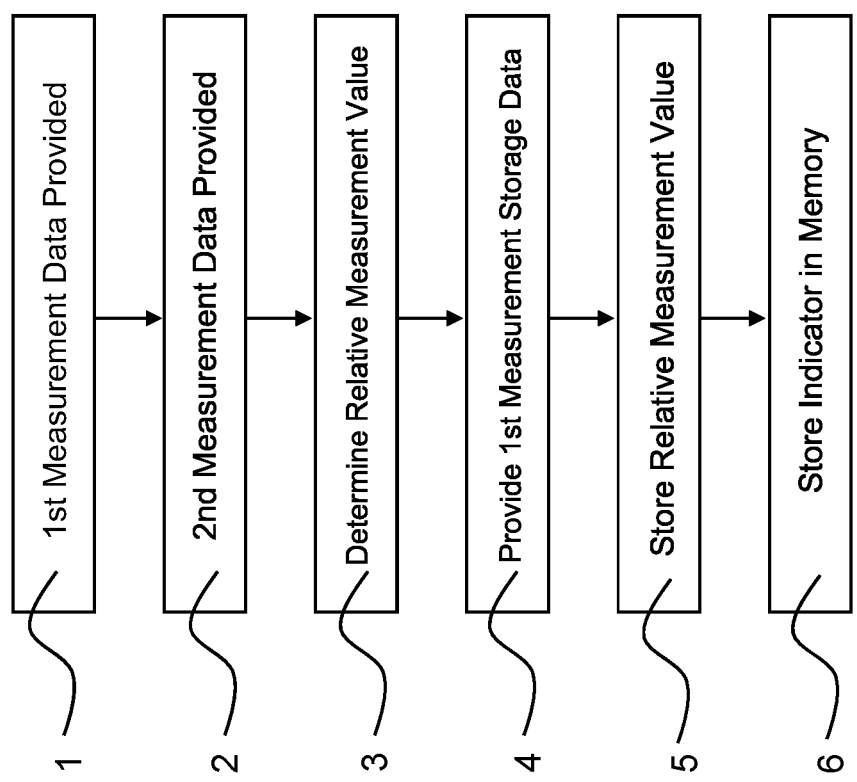
FIG. 1 is a schematic block diagram of a method for storing measurement data detected by a sensor.

FIG. 1 shows a schematic block diagram of a method for storing measurement data detected by a sensor device, also referred to herein as a "sensor." In step 1, first measurement data are provided. The first measurement data are indicative of a first measurement value for an analyte in a sample of a body fluid measured by a sensor device. Next, second measurement data are provided (step 2). The second measurement data are indicative of a second measurement value for the analyte in the sample of the bodily fluid measured by the sensor. A relative measurement value is determined by the processor (step 3). The relative measurement value is indicative of a value difference between the first measurement value and the second measurement value. Further, first measurement storage data are provided in the memory (step 4). This step comprises storing the first measurement value being assigned to a first storage area having a first storage size in the memory. In a next step, relative measurement storage data are provided in the memory (step 5). This step comprises storing the relative measurement value in the memory. The relative measurement storage data is assigned to a second storage area having a second storage size in the memory. The second storage size in the memory is smaller than the first storage size. In step 6, an indicator is stored in the memory. The indicator is assigned to the relative measurement storage data in the memory and indicative of a characteristic of the relative measurement storage data.

Figure 2:
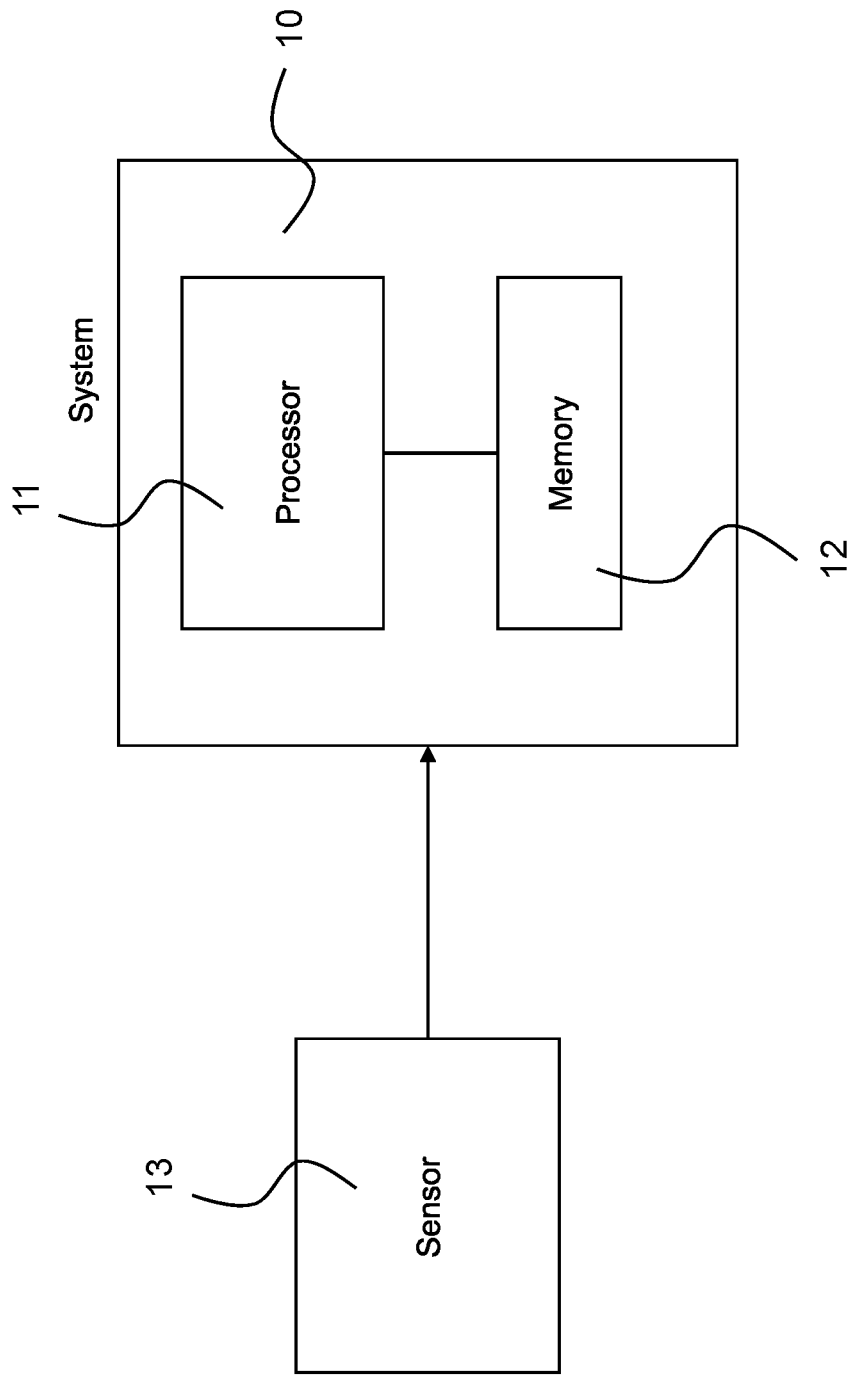
FIG. 2 is a schematic representation of a system having a processor and a memory, which is connected to a sensor device.

FIG. 2 shows a schematic representation of a system 10 having a processor 11 and a memory 12, which is connected to a sensor 13. The system 10 can be a continuous glucose monitoring system. The processor 11 is configured to determine a relative measurement value, which is indicative of a value difference between a first measurement value and a second measurement value measured by the sensor 13. The memory 12 is configured to store a value difference determined by the processor 11, an absolute value measured by the sensor 13, and an indicator assigned to the stored relative measurement storage data. The memory 12 can be a RAM or permanent memory, for example, Flash or EEPROM. The sensor 13 is configured to provide measurement values for an analyte in a sample of a bodily fluid. The sensor 13 may comprise an analyte sensor. The sensor 13 may measure glucose level of a patient. The sensor 13 may further be configured to transmit measurement values to the processor 11 and/or the memory 12. The processor 11 may further be configured to control insulin delivery based on the measurements provided by the sensor 13. The processor 11 and the memory 12 may be configured to communicate with each other.

The system 10 may be powered by a lithium battery with about 3 volt, alternatively with about 5 volt, in particular with a voltage between about 1 volt and about 12 volt.

Figure 3:
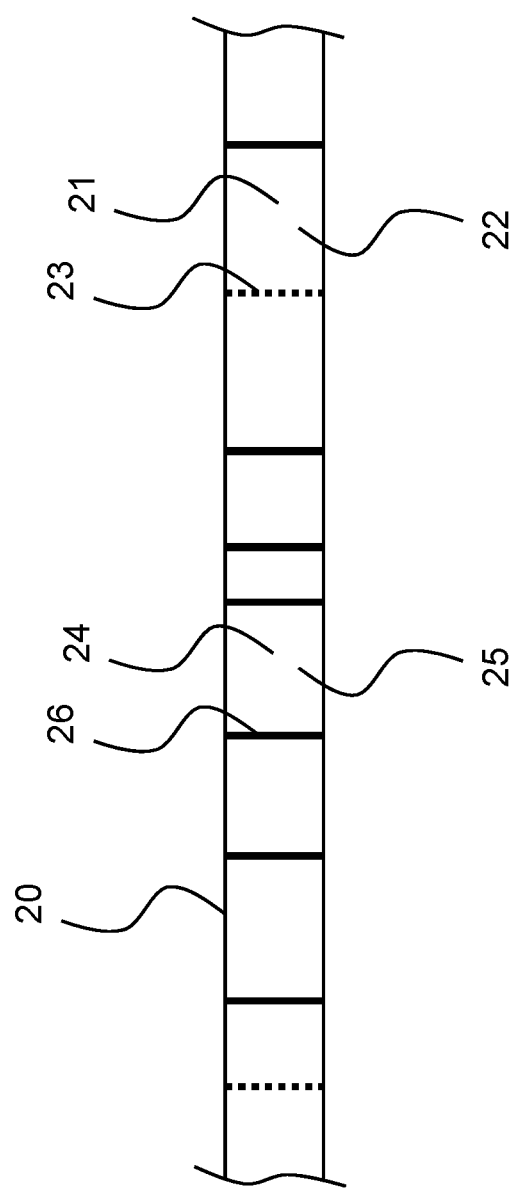
FIG. 3 is a schematic representation of storage data in a memory.

FIG. 3 shows a schematic representation of storage data 20 in a memory. The storage data 20 comprises a first measurement storage data 21 in the memory 12. The first measurement storage data 21 is related to a first storage area 22 having a first storage size. To the first storage area 22 a first measurement value is assigned. Further, the storage data 20 comprises a relative measurement storage data 24 in the memory. The relative measurement storage data 24 is related to a second storage area 25 having a second storage size. To the second storage area 25 a relative measurement value is assigned. The first and the relative measurement value may be related to the glucose level of a patient. The patient can be a human or an animal. In addition, the storage data 20 comprises an indicator 26 in the memory. The indicator 26 is assigned to the relative measurement storage data 24. Further, the storage data 20 may comprise an additional indicator 23 in the memory. The additional indicator 23 is assigned to the first measurement storage data 21. The storage data 20 may comprise one or several measurement storage data that are related to one or several measurement values. Further, the storage data 20 may comprise one or several additional indicators being assigned to the one or the several measurement values. Moreover, the storage data 20 may comprise one or several relative measurement storage data that are related to one or several relative measurement values. The storage data 20 may further comprise one or several indicators being assigned to the one or the several relative measurement values.

In an exemplary embodiment, the first measurement storage data 21 comprise, for example, eight measurement values. The first measurement storage data 21 may comprise the eight measurement values. The relative measurement storage data 24 may comprise the eight measurement values. Further measurement data or the further relative measurement data may comprise values indicative of the eight measurement values. Each minute the first measurement storage data 21 comprising eight measurement values may be detected by the sensor 13 and received in the memory 12. Further, each minute the measurement data comprising eight measurement values may be stored in the memory 12 as relative measurement values or as absolute measurement values.

The eight measurement values may be selected from the following group: time in seconds since the start, a median of a current flowing into the sensor, a standard deviation, a sensor voltage median, a battery voltage, temperature of the device, BG value in mg/dl, alternatively in kg/l, as well as an error and event flags (each value being stored by, e.g., 10 bits, in particular by a number of bits in the range of 6 to 22, alternatively stored by more than 22 bits).

In an example, the measurement data may have a size of 96 bits, alternatively 10 bits to several kBits, alternatively more than 1 kBit.

The absolute values of the eight measurement values corresponding to the first measurement storage data 21 may be stored in or as a header. The eight values may be stored bit by bit in a consecutive order of data bits in the memory 12. For decompression, values in the header may be provided as the starter values. The second measurement storage data 24, in particular the absolute value of the second measurement value can be determined by the relative measurement data and the starter values in the header. Further measurement data, in particular the absolute values of the further measurement values can be determined by the further relative measurement data and the starter values in the header. The decompression may be a determining of the relative or the further relative measurement data.

By storing the relative measurement data and/or the further relative measurement data instead of the second measurement data and/or the further measurement data the measurement data stored may be compressed. Stored measurement data that are compressed may have a smaller size than measurement data that are decompressed. A compression algorithm may be different and may be adapted to each measurement value. The algorithm may at least add one bit in front of each measurement value stored, depending on the level of compression. These bits may be header bits.

In one embodiment the measurement data may be "Time in second since the start," A new measurement value may be stored every 60 seconds. Only one header bit, e.g., the additional indicator or the indicator, may be stored. This bit, e.g., corresponding to the additional indicator, may be 1 indicative of the characteristic of the first measurement data, in particular of the further measurement values of the further absolute measurement values. If the first bit is 1, it may mean that the 21 following bits contain the first measurement data or the further measurement value, in particular the absolute value of the first measurement value or of the further measurement value, e.g., the information "Time in second since the start." If the first bit is a 0, it may mean the relative measurement data, or alternatively, one of the further relative measurement data is stored. In this example the relative or the further relative measurement data may have the size of zero. Thus, the indicator can indicate that "Time in second since the start" is equal to the last value plus 60 seconds.

In a further embodiment, a median can be stored on 12 bits, from 0 to 100 nA in steps of 25 pA. 6 bits may be provided as the first storage area, thus may correspond to +31/−32 LSB (bit numbering) and to a range of +775 to −800 pA. The first threshold may comprise two limiting values being +775 and −800 pA. If the relative measurement value is in-between the limiting values, the header bit is set to 0 and may be the indicator. In this case the relative measurement value may be stored in the memory. If the relative measurement value is not in-between the limiting values, the header bit is set to 1 and may be the additional indicator. In this case the absolute value of a first or the further measurement data may be stored in the following 12 bits being the second storage area. More than one header bit and more than one threshold may be provided.

In another exemplary embodiment two header bits may be provided. If the header bits are 00, e.g., being the indicator, it may mean that the difference between the first measurement value and the second measurement value is zero. Thus, 2 bits may be stored in the memory instead of 12 bits. If the header bits are 01, e.g., being a further indicator, it may mean that the relative measurement value is stored on the next 4 bits with a possible range of +7/−8 LSB. Thus, 6 bits may be stored in the memory instead of 12 bits. If the header bits are 10, e.g., being a second further indicator, it may mean that the relative measurement value is stored on the next 7 bits with a possible rage of +70(63+7)/−71(64+8) LSB. Thus, 9 bits may be stored instead of 12 bits. If the header bits are 11, e.g., being the additional indicator, it may mean that the absolute value of first or the further measurement values is stored on the next 12 bits. In this case, the stored value may have no dependence on other measurement data stored.

The features disclosed in this specification, the figures and/or the claims may be material for the realization of this disclosure in its various embodiments, taken in isolation or in various combinations thereof.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A method for storing measurement data detected by a sensor and indicative of an analyte in a sample of a body fluid, comprising, in a system having a processor and a memory:
   dividing the memory into at least two pages, wherein a size of the at least two pages matches a page size of a flash or EEPROM memory;
   providing first measurement data indicative of a first measurement value for an analyte in a sample of a body fluid measured by a sensor, wherein each of the at least two pages in the memory comprises a header having the first measurement data, whereby each of the at least two pages is configured to be decoded independently;
   providing second measurement data indicative of a second measurement value for the analyte in the sample of the body fluid measured by the sensor;
   determining a relative measurement value by the processor, the relative measurement value being indicative of a value difference between the first measurement value and the second measurement value;
   providing first measurement storage data in the memory, comprising storing the first measurement value in a first storage area having a first storage size in the memory;
   providing relative measurement storage data in the memory, comprising storing the relative measurement value in the memory, the relative measurement storage data stored in a second storage area having a second storage size in the memory which is smaller than the first storage size; and
   storing an indicator in the memory, the indicator being assigned to the relative measurement storage data in the memory and indicative of a characteristic of the relative measurement storage data.

2. The method of claim 1, further comprising storing an additional indicator in the memory, the additional indicator being assigned to the first measurement storage data in the memory and indicative of a characteristic of the first measurement storage data.

3. The method of claim 1, wherein the providing of the first measurement storage data comprises storing an absolute value of the first measurement value.

4. The method of claim 1, further comprising storing the first measurement value, the relative measurement value, and the indicator bit by bit in a consecutive order of data bits.

5. The method of claim 4, wherein the second storage size is smaller by one or more bits than the first storage size.

6. The method of claim 1, wherein the indicator assigned to the relative measurement storage data is indicative of a number of data bits assigned to the second storage size in the memory.

7. The method of claim 1, wherein the indicator assigned to the relative measurement storage data is indicative of a data compression characteristic of the relative measurement storage data.

8. The method of claim 1, wherein the indicator is provided in a header information in the memory.

9. A system for storing measurement data detected by a sensor and indicative of an analyte in a sample of a body fluid, the system comprising a processor and a memory, the system configured to carry out the method of claim 1.

10. The method of claim 1, wherein the first measurement data and/or the second measurement data comprises more than one measurement value.

11. The method of claim 10, wherein the first measurement data and/or the second measurement data comprise a blood glucose value and a value selected from the group consisting of: orientation of the sensor, time in seconds since the start, median of a current flowing into the sensor, a standard deviation, a sensor voltage median, a battery voltage, temperature of the device and an event flag.

* * * * *